United States Patent
Kanesaka et al.

[11] Patent Number: 5,911,754
[45] Date of Patent: Jun. 15, 1999

[54] FLEXIBLE STENT WITH EFFECTIVE STRUT AND CONNECTOR PATTERNS

[75] Inventors: Nozomu Kanesaka; George A. Tashji, both of Hillsdale, N.J.

[73] Assignee: Uni-Cath Inc., Saddle Brook, N.J.

[21] Appl. No.: 09/121,815

[22] Filed: Jul. 24, 1998

[51] Int. Cl.⁶ .................................................. A61F 2/02
[52] U.S. Cl. ................................................ 623/1; 606/198
[58] Field of Search .................................. 606/194, 195, 606/198; 623/1

[56] References Cited

U.S. PATENT DOCUMENTS

| | | | |
|---|---|---|---|
| 5,102,417 | 4/1992 | Palmaz | 606/195 |
| 5,449,373 | 9/1995 | Pinchasik et al. | 606/198 |
| 5,591,197 | 1/1997 | Orth et al. | 606/198 |
| 5,669,932 | 9/1997 | Fischell et al. | 606/198 |
| 5,697,971 | 12/1997 | Fischell et al. | 623/1 |
| 5,776,161 | 7/1998 | Globerman | 623/1 |
| 5,776,183 | 7/1998 | Kanesaka et al. | 606/198 |
| 5,800,521 | 9/1998 | Orth | 606/198 |
| 5,800,526 | 9/1998 | Anderson et al. | 606/198 |
| 5,807,404 | 9/1998 | Richter et al. | 623/1 |
| 5,810,872 | 9/1998 | Kanesaka et al. | 606/198 |
| 5,824,043 | 10/1998 | Cottone, Jr. | 606/195 |
| 5,836,964 | 11/1998 | Richter et al. | 623/1 |
| 5,843,120 | 12/1998 | Israel et al. | 606/198 |

*Primary Examiner*—Paul J. Hirsch
*Attorney, Agent, or Firm*—Kanesaka & Takeuchi

[57] ABSTRACT

A stent for the reinforcement of a blood vessel which comprises a plurality of circularly arranged elongated struts inclined in the same direction relative to an imaginary line on the outer surface of the circularly dimensioned stent. The struts include joint members for joining adjacent elongated struts within the same circular row in a continuous manner. Connector members are formed to the joint members and include a verticle, relative to the longitudinal axis of the stent, portion to which oppositely extending end portions connect to adjacent rows of the joint members of the circumferentially arranged joint members of the elongated members so that the connectors provide flexibility along the longitudinal axis and reduce longitudinal movement of the stent when the stent is expanded.

6 Claims, 3 Drawing Sheets

FLEXIBLE STENT WITH EFFECTIVE STRUT AND CONNECTOR PATTERNS

BACKGROUND OF THE INVENTION AND RELATED ART STATEMENT

The present invention relates to a stent with effective strut and connector patterns.

"Stent" is known in the art as a prosthesis or graft used for reinforcing the blood vessel, such as an artery, or for maintaining patency of the blood vessel after opening a stenosis in the artery, and has been effectively used in the vascular treatment in place of surgical exposing, incising, removing, replacing or bypassing a defected blood vessel required in the conventional vascular surgery.

The stent is generally formed into a cylindrical shape, and functions to support a part of the patient's blood vessel or another anatomical lumen from the inside thereof so as to maintain the patency of the artery or to reinforce a dissected arterial wall or like, which may impede a fluid passageway by collapse thereof. According to the recent clinical data, it has been reported that occurrence of re-stenosis can be greatly reduced by using the stent after opening the stenosis by the PTCA (percutaneous transluminal coronary angioplasty) balloon catheter.

In the conventional stents, the followings have been considered in constructing and using the stents. Firstly, in the balloon expandable type of the stent, the stent in a closed condition is mounted on a balloon attached at a distal end portion of a balloon catheter, and delivered to a lesion or stenosis through the patient's meandering artery over a guide wire preliminary introduced in the artery. In this respect, the stent should be flexible in order to be delivered through the narrow and meandering artery. On the other hand, the expanded stent should have enough strength to support the dissected arterial wall sufficiently or to keep opening stenosis. Therefore, it is desired that the stent is flexible, has a sufficient support structure, and can expand to have a large diameter.

Secondly, as disclosed in U.S. Pat. No. 5,669,932, when the stent is deployed by expanding the balloon of the balloon catheter, the entire length of the deployed stent becomes shorter than the length of the closed stent. The deployed length of the stent may be checked if it is adequate to cover a particular length of the stenosis. However, it is desirable to prevent shortening of the length of the expanded stent because the shortening may not cover the lesion as a doctor planed for the treatment.

Accordingly, one object of the invention is to provide a flexible stent which can be easily delivered through the meandering and narrow artery.

Another object of the invention is to provide the stent as stated above, which can substantially prevent shortening of the entire length of the stent when it is expanded.

A further object of the invention is to provide the stent as stated above, which can prevent twisting of the stent when it is expanded, to thereby prevent damage of cells due to twisting of the stent.

Further objects and advantages of the invention will be apparent from the following description of the invention.

SUMMARY OF THE INVENTION

To achieve the aforementioned objects, the present invention provides an expandable stent, which is formed of a plurality of rows of circularly arranged elongated members situated side by side in a longitudinal axis, and a plurality of rows of circularly arranged connectors situated between two adjacent rows of the circularly arranged elongated members for connecting the same. Each row of the elongated members includes first and second elongated members disposed on an imaginary circular surface and inclining in a same side relative to a line extending on the imaginary circular surface parallel to the longitudinal axis, and joint portions respectively connecting ends of the first and second elongated members so that the first and second elongated members extend continuously through the joint portions.

Each connector has a vertical portion substantially perpendicular to the line extending on the imaginary circular surface, and upper and lower end portions extending laterally in opposite directions from ends of the vertical portion. The upper and lower end portions are connected to the joint portions in the two adjacent rows of the circularly arranged elongated members. The connectors provide flexibility to the stent along the longitudinal axis and reduce the longitudinal movement of the stent when the stent is expanded.

In the closed condition of the stent, each vertical portion of the connector extends in the direction substantially perpendicularly to the line on the imaginary circular surface parallel to the longitudinal axis of the stent, and the upper and lower end portions extend laterally in the opposite directions. Thus, the stent can be relatively easily bent in the longitudinal direction. When the stent is delivered through the winding and narrow artery, the stent can be easily bent at the connectors to provide great flexibility.

Also, when the stent is expanded, the vertical portion is moved to orient in the direction substantially parallel to the longitudinal axis. Due to the movement of the vertical portion, when the stent is expanded, the elongated members are liable to rotate or twist in the artery, but the rotation or twisting of the stent is substantially prevented. Thus, the damage to the cells in the artery when the stent is expanded is reduced. Further, when the elongated members are expanded, the stent is generally shortened in the axial direction, but since the vertical portions are oriented laterally, the length of the stent does not substantially change to prevent shortening of the entire length of the expanded stent.

Still further, since only one of the pairs of the elongated members is substantially pivoted when the stent is expanded, the stent can be easily expanded.

Also, in the stent of the invention, the upper end portion of the connector is attached to an upper end of the joint portion in one circularly arranged elongated members, and the lower end portion of the connector is attached to a lower end of the joint portion in another circularly arranged elongated members situated adjacent thereto. The upper end and the lower end are laterally and vertically spaced apart from each other.

Preferably, each of the end portions of the connector is curved to project outwardly so that when the stent is expanded, the first elongated members are pivoted at the joint portions and the vertical portions are moved horizontally.

Also, each of the first elongated members is preferably shorter than each of the second elongated members, and the first and second elongated members are arranged alternately and inclined obliquely.

DETAILED DESCRIPTION OF PREFERRED EMBODIMENTS

An embodiment of the present invention is explained with reference to the attached drawings.

Figure 1:
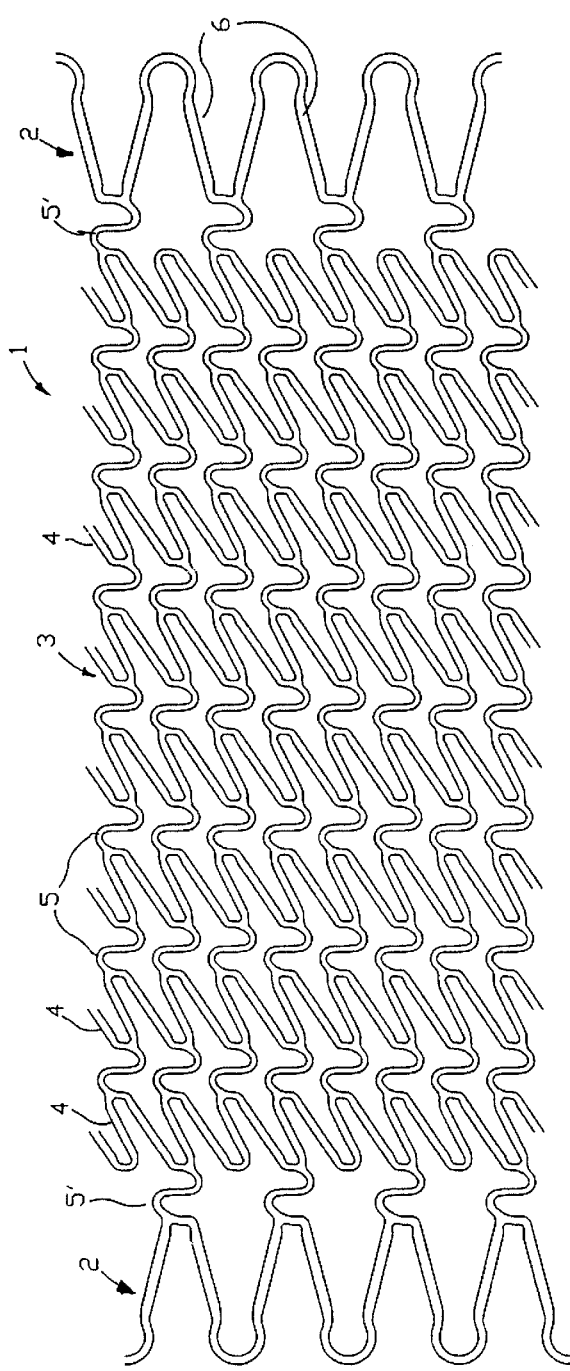
FIG. 1 is a plan view of a flexible stent with effective strut and joint patterns according to the present invention, wherein the stent is shown in a flat sheet form.
Figure 2:
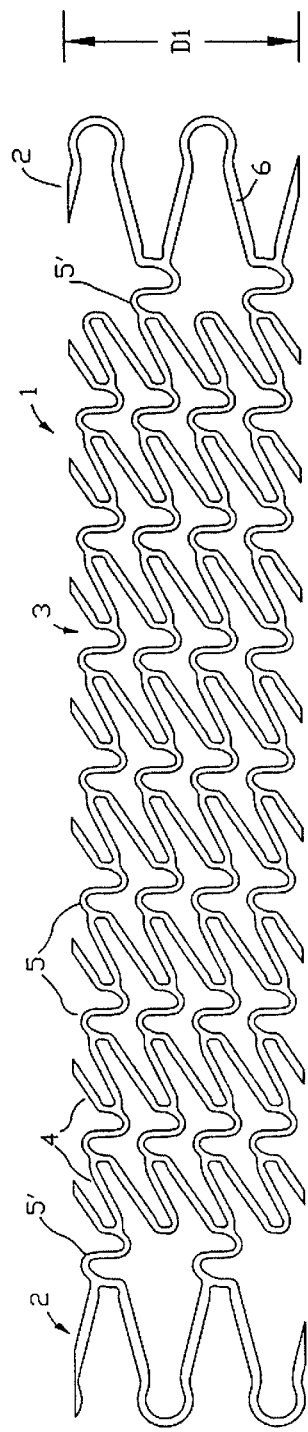
FIG. 2 is a side view of the stent before it is expanded.

Numeral 1 designates a stent, shown in a flat form in FIG. 1. The stent 1 is formed of two large mesh portions 2 located at both longitudinal ends of the stent 1, and a small mesh portion 3 disposed between the large mesh portions 2. The small mesh portion 3 and the large mesh portions 2 are integrally formed with each other to form a circular or cylindrical shape along the longitudinal axis of the stent 1, as shown in FIG. 2. The stent has the diameter D1.

The small mesh portion 2 is formed of plural rows of struts 4, and plural rows of connectors 5, and each row of the struts 4 and each row of the connectors 5 are circularly arranged in the longitudinal axis of the stent 1. Each row of the connectors 5 is adjacent to each row of the struts 4. Namely, the rows of the connectors 5 and the rows of the struts 4 are arranged alternately as shown in the figures.

Figure 3:
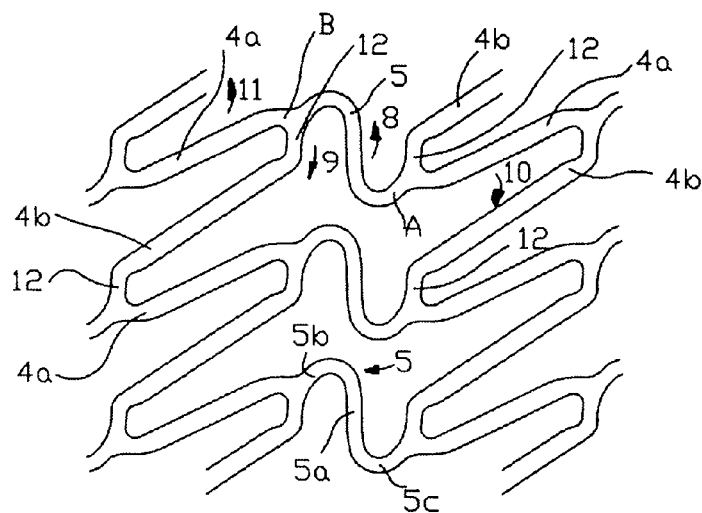
FIG. 3 is a magnified plan view of a part of the stent shown in FIG. 1, showing a pattern of a small mesh portion in detail.
Figure 4:
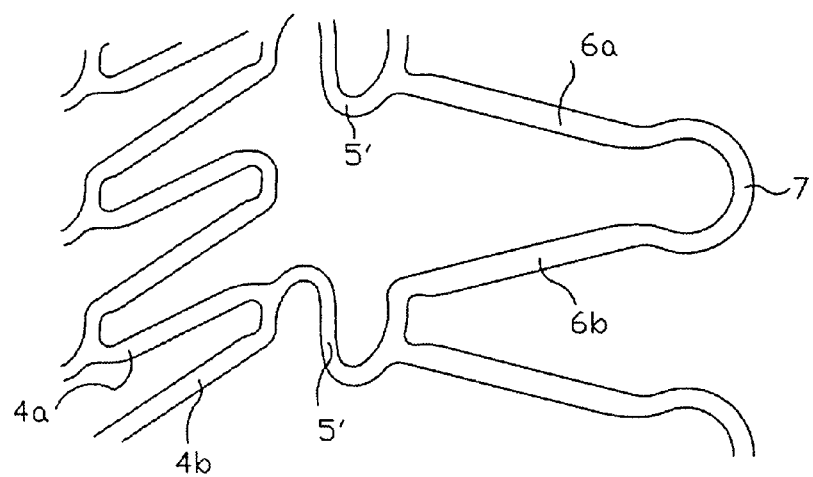
FIG. 4 is a magnified plan view of an end portion of the stent shown in FIG. 1, showing a pattern of a large mesh portion in detail.

As shown in FIG. 3, each row of the struts 4 is formed of pairs of struts 4, each being formed of a first strut 4a and a second strut 4b, and a joint portion 12 for connecting ends of the first strut 4a and the second strut 4b. The first and second struts 4a, 4b incline obliquely with respect to an imaginary line on the surface of the stent extending parallel to the longitudinal axis of the stent 1. The first and second struts 4a, 4b are arranged alternately in the row, and the joint portions 12 connect ends of the first and second struts 4a, 4b. More specifically, the joint portion 12 connects one end of the first strut 4a with one end of the second strut 4b, and then another joint portion 12 connects the other end of the second strut 4b and an end of another first strut 4b. Accordingly, the first struts 4a and the second struts 4b alternately arranged and connected by the joint portions 12 extend continuously in each row. Incidentally, in the embodiment, the first strut 4a is shorter than the second strut 4b.

Each connector 5 has an inclined S-shape, and includes a vertical portion 5a extends substantially perpendicularly to the imaginary line on the surface of the stent 1 and upper and lower ends 5b, 5c extending laterally relative to the vertical portion 5a. Namely, each of the upper and lower ends 5b, 5c of the connector 5 is curved to project laterally and outwardly from the vertical portion 5a. When the stent 1 is expanded, the first struts 4a are pivoted at the joint portions 12, and the vertical portions 5a are moved horizontally.

As shown in FIG. 3, for example, the lower end 5c of the S-shaped connector 5 is connected to the joint portion 12 at a point A, i.e., to the joint portion 12 connecting the ends of the second strut 4b and the first strut 4a in one row (right row in FIG. 3), and the upper end 5b of the S-shaped connector 5 is connected to the joint portion 12 at a point B, i.e., the joint portion 12 connecting the ends of the first struts 4a and the second strut 4b in another row (left row in FIG. 3). The point A, that is, the connection point between the lower end 5c of the connector 5 and the joint portion 12, is located closer to the first strut 4a in the right row, and the point B, that is, the connection point between the upper end 5b of the connector 5 and the joint portion 12, is located closer to the first strut 4a in the left row. When the stent 1 is expanded, the upper end 5b and the lower end 5c are moved to close to each other while the vertical portion 5a is oriented generally horizontally.

Each large mesh portion 2 is formed of one row of elongated struts 6 which are longer than the struts 4, and a row of connectors 5'. The row of the connectors 5' includes fewer connectors 5' than those of each row of the connectors 5 in the small mesh portion 3. The row of the elongated struts 6 is disposed at the end of the stent 1, and the row of the connectors 5' is located between the row of the elongated struts 6 and the row of the struts 4 as shown in FIGS. 1 and 2.

The row of the elongated struts 6 is formed of pairs of elongated struts 6a, 6b, and end connectors 7, wherein a first elongated strut 6a is connected to a second strut 6b by the end connector 7 at an end of the stent 1. The first elongated strut 6a is inclined obliquely along the imaginary line on the outer surface of the stent 1 and extends symmetrically to the second elongated strut 6b. The first and second elongated struts 6a, 6b are connected to the respective ends of the S-shaped connectors 5' at the respective other ends thereof. In the embodiment, the connector 5' has the same size and shape as the connector 5, but the number of the connectors 5' in one row is fewer in the row of the connectors 5'. The connector 5' are connected to the struts 4. In the row of the struts 4 adjacent to the row of the connectors 5', one in two struts 4 adjacent to each other is not connected to the connector 5' as shown in the figures.

In use, the stent 1 in a closed condition shown in FIG. 2 is placed over a balloon of a balloon catheter (not shown), which is known in the art, and then the balloon catheter with the stent 1 is introduced into the patient's artery over a guide wire (not shown), which is preliminary introduced into the artery, so as to locate the stent 1 at a lesion or stenosis of the artery. Then, the balloon is inflated to expand the stent as well as the stenosis to have patency in the artery, and the balloon catheter is withdrawn from the artery over the guide wire.

Figure 5:
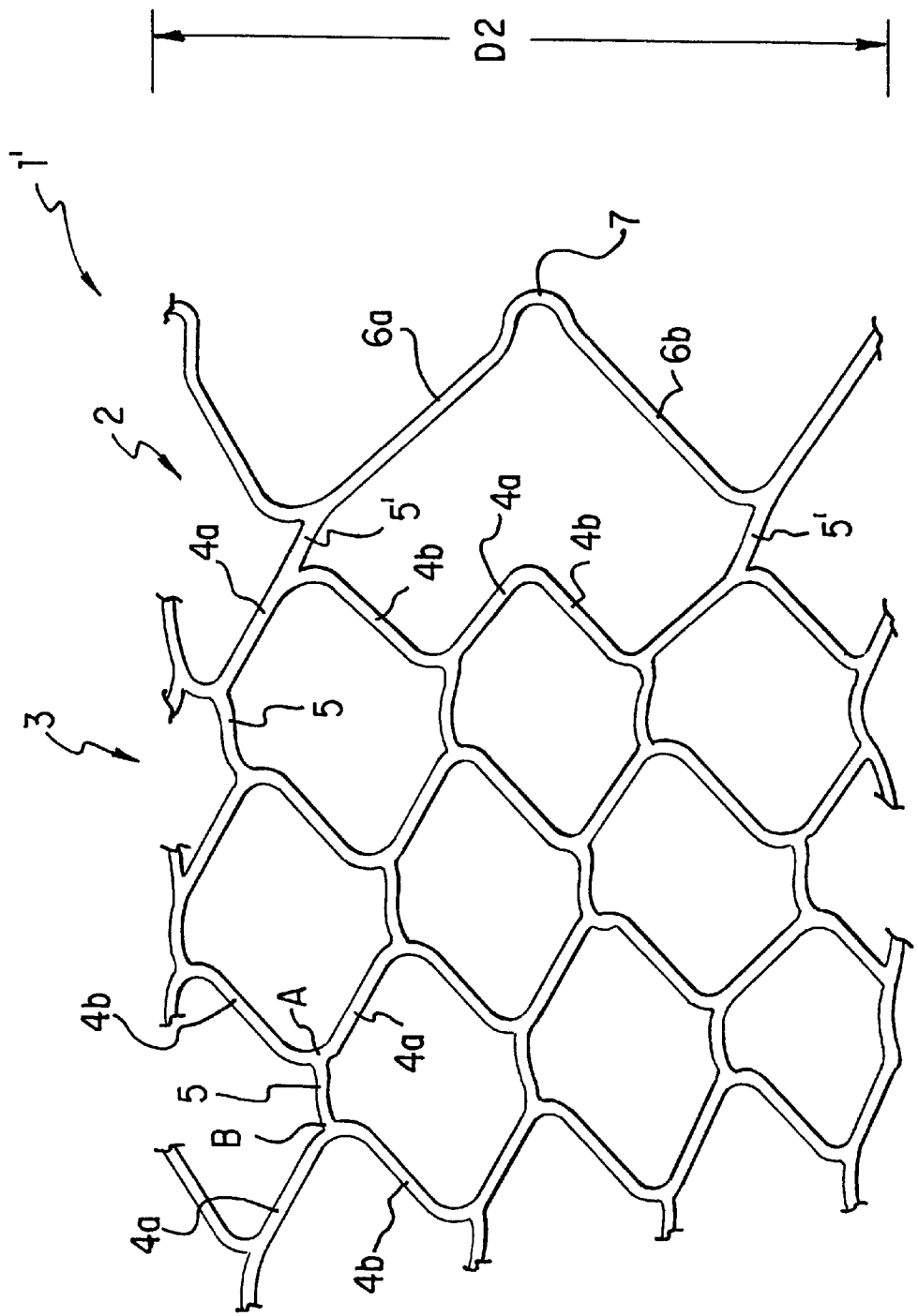
FIG. 5 is a magnified side view of a part of the stent after it is expanded.

When the stent 1 is expanded by the balloon catheter, the stent 1 having the diameter D1 in the closed condition as shown in FIG. 2 is expanded to the diameter D2 as shown in FIG. 5, wherein the diameter D2 is greater than the diameter D1.

In particular, when the stent 1 is expanded, the lower end 5c of the connector 5 at the point A moves upwardly as shown by an arrow 8 in FIG. 3, and the upper end 5b of the connector 5 at the point B moves downwardly as shown by an arrow 9 in FIG. 3. Therefore, the vertical portion 5a of the connector 5 extends substantially horizontally along the imaginary line on the surface of the stent parallel to the longitudinal axis of the stent 1. Since the upper and lower ends 5b, 5c are moved toward the imaginary line, the movement or twisting of the struts are substantially prevented. Thus, the damage of the cells in the artery is prevented.

Also, since the vertical portions 5a of the connectors 5 are oriented laterally when the stent 1 is expanded, the longitudinal length of the rows of the connectors 5 becomes longer than that of the connectors 5 in the closed stent 1. However, when the stent 1 is expanded, the struts 4 which extend substantially parallel to each other in the closed condition are pivoted, so that the longitudinal length of the struts 4 becomes shorter than the longitudinal length of the rows of the struts 4 in the closed condition, as explained in the conventional stents. Expansion and reduction of the stent are substantially the same. Therefore, the total longitudinal length of the expanded stent is almost the same as that of the closed stent. Shortening the length of the stent at the time of expansion can be prevented.

Also, as shown in FIG. 3, when the stent 1 with the first and second struts 4a, 4b are expanded, the first struts 4a are substantially moved away from the second struts 4b, i.e. toward the directions shown by arrows 10, 11, respectively, resulting in the mesh-like structure as shown in FIG. 5. Since one of the struts in the pair is substantially expanded to deploy the stent, a large force is not required to expand the stent as compared to the conventional stents.

Also, in the present invention, since the vertical portions 5a are oriented perpendicularly to the longitudinal direction of the stent, when the stent 1 is introduced through the winding and narrow artery, the stent 1 can be bent at the end portions of the connectors 5. Thus, the stent of the invention has great flexibility.

Further, in the present invention, since the expanded stent has a mesh-like pattern (referring to FIG. 5), the expanded stent has an enough strength to hold and maintain the patency of the artery after the stenosis is opened by the balloon, resulting in preventing re-stenosis.

While the invention has been explained with reference to the specific embodiments of the invention, the explanation is illustrative and the invention is limited only by the appended claims.

What is claimed is:

1. An expandable stent comprising:
    a plurality of rows of circularly arranged elongated members situated side by side in a longitudinal axis, each row of the elongated members including first and second elongated members disposed on an imaginary circular surface and inclining in a same direction relative to an imaginary line extending on the imaginary circular surface parallel to the longitudinal axis, and joint portions, each joint portion connecting ends of the first and second elongated members so that the first and second elongated members extend continuously through the joint portions, and
    a plurality of rows of circularly arranged connectors situated between two adjacent rows of the circularly arranged elongated members for connecting the same, each connector having a vertical portion substantially perpendicular to the imaginary line extending on the imaginary circular surface and upper and lower end portions extending laterally in opposite directions from ends of the vertical portion, said upper and lower end portions being connected to the joint portions in the two adjacent rows of the circularly arranged elongated members so that the connectors provide flexibility along the longitudinal axis and reduce longitudinal movement of the stent when the stent is expanded.

2. An expandable stent according to claim 1, wherein the upper end portion of the connector is attached to an upper end of the joint portion in one set of the circularly arranged elongated member, and the lower end portion of the connector is attached to a lower end of the joint portion in another set of the circularly arranged elongated members situated adjacent thereto, said upper end and lower end being laterally and vertically spaced apart from each other.

3. An expandable stent according to claim 2, wherein each of the end portions of the connector is curved to project outwardly so that when the stent is expanded, the first elongated members are pivoted at the joint portions and the vertical portions are moved horizontally.

4. An expandable stent according to claim 2, wherein each of said first elongated members is shorter than each of said second elongated members, said first and second elongated members being arranged alternately and inclining obliquely.

5. An expandable stent according to claim 2, further comprising large mesh end portions provided at both ends of the stent, each of the large mesh portions being formed of a row of a plurality of circularly arranged elongated members, and a row of a plurality of second connectors, said each row of the plurality of elongated members including a plurality of third and forth elongated members arranged alternately and symmetrically inclining with respect to the imaginary line extending on the imaginary circular surface, end connectors for connecting ends of the third and fourth elongated members to define the ends of the stent, and second joint portions for connecting ends of the third and fourth elongated members so that the third and forth elongated members extend continuously through the second joint portions, each of said second connectors being formed of a vertical portion extending substantially perpendicular to the imaginary line on the imaginary circular surface parallel to the longitudinal axis and upper and lower ends protruding outwardly from ends of the vertical portion in opposite directions of the longitudinal axis, said each upper end of the second connector being connected to the upper end of the joint portion for connecting the first and second elongated members in adjacent row, said each lower end of the second connector being connected to a lower end of the joint portion connecting the third and fourth elongated members.

6. An expandable stent according to claim 5, wherein the third and fourth elongated members are longer than the first and second elongated members so that when the stent is expanded, the both ends of the stent has a larger mesh pattern than a middle portion of the stent.

\* \* \* \* \*